(12) United States Patent
Koerner

(10) Patent No.: US 12,329,440 B2
(45) Date of Patent: Jun. 17, 2025

(54) CUTTING ELECTRODE, SURGICAL INSTRUMENT AND METHOD FOR MANUFACTURING THE CUTTING ELECTRODE

(71) Applicant: Erbe Elektromedizin GmbH, Tuebingen (DE)

(72) Inventor: Johannes Koerner, Wangen im Allgaeu (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 924 days.

(21) Appl. No.: 16/987,145

(22) Filed: Aug. 6, 2020

(65) Prior Publication Data
US 2021/0045802 A1 Feb. 18, 2021

(30) Foreign Application Priority Data

Aug. 14, 2019 (EP) ..................... 19191757

(51) Int. Cl.
*A61B 18/14* (2006.01)
*B29C 45/00* (2006.01)
(Continued)

(52) U.S. Cl.
CPC ...... *A61B 18/1445* (2013.01); *B29C 45/0053* (2013.01); *B29C 45/14065* (2013.01); *B29C 45/14336* (2013.01); *A61B 2017/00526* (2013.01); *A61B 2018/00601* (2013.01); *B29K 2083/00* (2013.01); *B29K 2995/0005* (2013.01); *B29L 2031/72* (2013.01)

(58) Field of Classification Search
CPC ...... A61B 18/1445; A61B 2017/00526; A61B 2018/00601; B29C 45/0053; B29C 45/14065; B29C 45/14336; B29K 2083/00; B29K 2995/0005; B29L 2031/72
See application file for complete search history.

(56) References Cited

U.S. PATENT DOCUMENTS

| | | | |
|---|---|---|---|
| 4,315,444 A * | 2/1982 | Perrino | ............... H02G 1/1214 29/415 |
| 6,247,986 B1 | 6/2001 | Chiu et al. | |

(Continued)

FOREIGN PATENT DOCUMENTS

| | | |
|---|---|---|
| EP | 0 852 480 B1 | 8/2003 |
| EP | 1 958 583 A2 | 8/2008 |

(Continued)

*Primary Examiner* — Michael F Peffley
*Assistant Examiner* — Bo Ouyang
(74) *Attorney, Agent, or Firm* — Blank Rome LLP

(57) ABSTRACT

A method for manufacturing a cutting electrode for a surgical instrument. The method involves starting with a material blank that is provided with a rated break location. The material blank is dimensioned to allow for separation with forces sufficiently low that they can also be transmitted by the plastic body. The rated break location separates the material blank in a first section serving exclusively for handling and positioning of the material blank in a mold as well as in a second section that self-supportingly projects in a mold hollow space and is overmolded by plastic. After removal, the first section can be easily broken off the cutting electrode. The created breaking edge forms a cutting edge.

19 Claims, 4 Drawing Sheets

(51) Int. Cl.
  *B29C 45/14* (2006.01)
  *A61B 17/00* (2006.01)
  *A61B 18/00* (2006.01)
  *B29K 83/00* (2006.01)
  *B29L 31/00* (2006.01)

(56) References Cited

U.S. PATENT DOCUMENTS

| | | | |
|---|---|---|---|
| 8,394,094 B2 | 3/2013 | Edwards et al. | |
| 8,740,901 B2 | 6/2014 | Johnson et al. | |
| 8,936,595 B2 | 1/2015 | Mitzlaff et al. | |
| 10,130,414 B2 * | 11/2018 | Weiler | A61B 18/1445 |
| 2009/0254081 A1 * | 10/2009 | Allison | A61B 18/1442 |
| | | | 29/469 |
| 2009/0320268 A1 * | 12/2009 | Cunningham | A61B 18/1445 |
| | | | 29/244 |
| 2011/0073246 A1 * | 3/2011 | Brandt | C23F 1/02 |
| | | | 156/379 |
| 2011/0135862 A1 | 6/2011 | Sumi et al. | |
| 2016/0249975 A1 | 9/2016 | Konishi et al. | |
| 2019/0185370 A1 * | 6/2019 | Cheng | C03C 3/064 |

FOREIGN PATENT DOCUMENTS

| | | |
|---|---|---|
| EP | 2 617 378 A1 | 7/2013 |
| EP | 2 959 854 A1 | 12/2015 |
| EP | 3 132 765 A1 | 2/2017 |
| JP | S5711030 A | 1/1982 |
| JP | H03214774 A | 9/1991 |
| JP | 2001320152 A | 11/2001 |
| JP | 201121246 A | 2/2011 |
| JP | 2011020162 A | 2/2011 |
| JP | 20167542 A | 1/2016 |
| RU | 2506903 C2 | 2/2014 |
| RU | 2015124783 A | 1/2017 |
| WO | WO 2011/083027 A1 | 7/2011 |

* cited by examiner

CUTTING ELECTRODE, SURGICAL INSTRUMENT AND METHOD FOR MANUFACTURING THE CUTTING ELECTRODE

CROSS REFERENCE TO RELATED APPLICATION

This application claims priority to European patent application No. 19191757.4, filed Aug. 14, 2019, the subject matter of which is incorporated by reference herein in its entirety.

TECHNICAL FIELD

The invention refers to a method for manufacturing a cutting electrode for a surgical instrument, for example a dissection electrode of a fusion and dissection instrument, as well as the cutting electrode and a surgical instrument comprising the respective cutting electrode, manufactured by the method.

BACKGROUND

U.S. Pat. No. 8,740,901 B2 discloses a surgical instrument for sealing and cutting vessels, i.e. for tissue fusion and dissection, in which the tissue sealing also the tissue dissection is carried out electrically. Sealing electrodes defined at flanges of two jaw members serve for tissue sealing that conduct a current through tissue clamped between the flanges that heats and coagulates thereby. In this manner vessels clamped by the instrument can be closed. A dissection electrode accommodated in one of the jaw members thereby serves for vessel dissection. The dissection electrode can be embedded in an insulation material with different depths depending on the embodiment, such that only the narrow side of the dissection electrode and parts of its flat sides are accessible.

EP 0 852 480 B1 shows a scalpel-like electrosurgical instrument, the flat and spatula-shaped electrode is provided on its two flat sides with a thick insulating coating. This coating covers also the narrow sides, however, is relatively thin there. Accordingly, a radio frequency current originating from the instrument shall predominantly flow through the edges of the instrument.

Such an instrument is also known from EP 3 132 765 A1. It comprises an insulation body in its upper jaw member provided with a dissection electrode, the insulation body comprising centrally a narrow wall section aligned toward a counter support of the opposed jaw member. The dissection electrode is embedded in the narrow side of this wall section.

The configuration of an insulation body with dissection electrode is basically also apparent from US 2016/0249975 A1. The dissection electrode is formed by narrow strip-like metal portions that have different ohmic resistances.

Additional prior art is formed by U.S. Pat. No. 8,394,094 B2. It proposes to support a dissection electrode between two insulating elements that cover the flat sides of the dissection electrode and leave the narrow side of the dissection electrode uncovered.

The trend seen in surgical instruments goes to filigree, but however very powerful and reliably operating instruments. Such instruments generally must create a cut as precise as possible in short time. This with as low current as possible, in order to be able to concurrently carry out a tissue coagulation. Particularly in cases in which the coagulation electrodes and the dissection electrode are fed concurrently from one and the same generator with limited power, it can be of some importance to achieve an energy-saving cut.

It has turned out that thereby the geometry of the cutting electrode and its insulation is decisive. Corresponding cutting electrodes, however, are difficult to manufacture.

SUMMARY

Starting therefrom it is the object of embodiments of the invention to provide a method for manufacturing of a cutting electrode, for example a dissection electrode.

This object is solved, for example, with the method according to claim 1:

This inventive method is based on providing a flat material blank from an electrically conductive material, preferably a metal sheet blank that comprises a section forming the subsequent electrode as well as a section only serving for handling. The material blank is provided with a rated break location that separates it into the first and second sections. The first section only serves for handling, while the second section forms the subsequent electrode. The material blank is, for example, a thin metal sheet, the thickness thereof can have a range of fractions of a 1/10 mm up to multiple 1/10 mm depending on the application. In a preferred embodiment the thickness has an amount of 0.1 mm. The metal can be steel, wherein the steel is preferably not ductile, particularly not plastically deformable.

The rated break location is preferably formed by a line-like zone in which the thickness of the sheet metal blank is reduced. The thickness reduction can be formed by a straight or arc-shaped groove that extends along one flat side of the material blank, preferably from one edge to another edge thereof. Alternatively, also two notches or grooves can be provided that are arranged at the two opposed flat sides of the material blank and have the same position and the same course. In other words, they are orientated parallel to each other and define a area that is orthogonal to the flat sides of the material blank.

The rated break location can be created by grinding, milling, etching, embossing, roller burnishing or similar methods that are suitable to decrease the thickness of the material blank locally. Moreover, it is also possible to form the rated break location by a series of perforations or slots or by a local material modification, e.g. by a local material embrittlement. The local material embrittlement can be thermally caused, e.g. by local laser hardening.

In the next step the material blank having the rated break location is inserted in the engraving of a mold that encloses the first section with contact, such that the second section projects in a cavern or hollow space of the mold. Thereby the mold is preferably configured such that the rated break location is positioned exactly at the edge of the hollow space. In the next step plastic is inserted into the mold, such that it flows around the second section and potentially permeates through the perforation provided in the second section. Thus, a form fit between the plastic body and the second section is obtained. The preferred molding process is injection molding.

After opening of the mold and removing the plastic body with the material blank held therein, the first section of the material blank is broken at the rated break location of the second section, e.g. by hand or by means of a forceps or another suitable tool. Along the margin of the plastic body a breaking edge is formed at which the second section of the material blank remains uncovered as finished cutting edge.

The cutting edge is rough due to breaking and it does not require postprocessing. Damages or stresses of the plastic body due to subsequent processing steps are minimized. The metal sheet of the cutting electrode is preferably symmetrically arranged in the plastic body.

The method allows creation of an electrically conductive, nearly line-like preferably metallic cutting edge directly at the plastic body that can be configured in one-part or multiple-part form, without the need that parts of the flat side of the cutting electrode have to remain uncovered. For the separation of the first section no surface areas have to be accessible for grippers, forceps or the like. The cutting edge can terminate flush with the plastic body or project very slightly beyond the plastic body or can also terminate slightly below the adjoining surfaces of the plastic body. The manufacturing is thus simple and makes high quality possible in a process reliable manner and allows the creation of highest cutting qualities, due to the restriction of the current on a narrow breaking edge of the cutting electrode. Thereby the cutting electrode can consist of metal or an electrically conductive ceramic. Embodiments of the inventive method allow the particularly precise manufacturing of the cutting electrode in which the electrode is centrally embedded in the plastic body such that plastic walls on both sides of the electrode have the same thickness.

If the first section of the material blank is at least as large as the second section, the handling during manufacturing and the subsequent separation of the first section from the remaining second section overmolded with the plastic body can be carried out very easily also manually.

If the first section is positioned by at least one and preferably at least two pins in correct position in the mold, a particularly reliable positioning of the material blank in the mold is obtained.

The rated break location is preferably configured as a narrow strip-like, i.e. line-like, area having reduced material thickness. It can be formed by grinding, roller burnishing or etching or otherwise of one side or both sides of the material blank. The area of reduced material thickness can be a groove. The groove can have a round, rectangular, trapezoid, triangular or arc-shaped cross-section. Independent from its shape the groove is preferably at least one third and further preferably half as deep as the thickness of the material blank. The groove depth as well as the thickness of the material blank have to be measured orthogonal to one flat side of the material thickness. If grooves are inserted from both sides in the material blank, their depth has an amount of preferably 1/6 to 1/4 of the thickness of the material blank.

The cutting electrode created with embodiments of the inventive method described above comprises a plastic body in which an electrode is embedded that emerged from the second section of the material blank. It comprises an uncovered breaking edge that forms the electrical cutting edge.

Preferably the plastic body consists of a flexible plastic, particularly an elastic plastic such as, e.g. silicone or of a silicone-like plastic, an elastomer or the like.

Preferably the electrode comprises a uniform constant thickness, wherein it can have a reduced thickness in direct proximity of the breaking edge such that a tapering zone is formed adjoining the breaking edge. This tapering zone contributes to the current concentration at the cutting edge such that a fast and proper cut can be achieved.

The plastic body is preferably configured to extend at least up to the tapering zone and further preferably to extend into the tapering zone or beyond the tapering zone such that the uncovered breaking surface of the electrode is preferably not larger than the cross-section surface of the cutting electrode. This means that the flanks of the electrode are preferably covered by plastic up to the breaking edge.

The plastic body comprises faces on both sides of the breaking edge, the width thereof is preferably smaller than the double of the thickness (width) of the electrode. This avoids a tissue contusion and a mechanical separation and ensures that the desired cut is completely or predominantly carried out electrically, but not mechanically.

BRIEF DESCRIPTION OF THE DRAWINGS

Further details of embodiments of the invention result from the drawings, the description or the claims. The drawings show:

DETAILED DESCRIPTION

Figure 1:
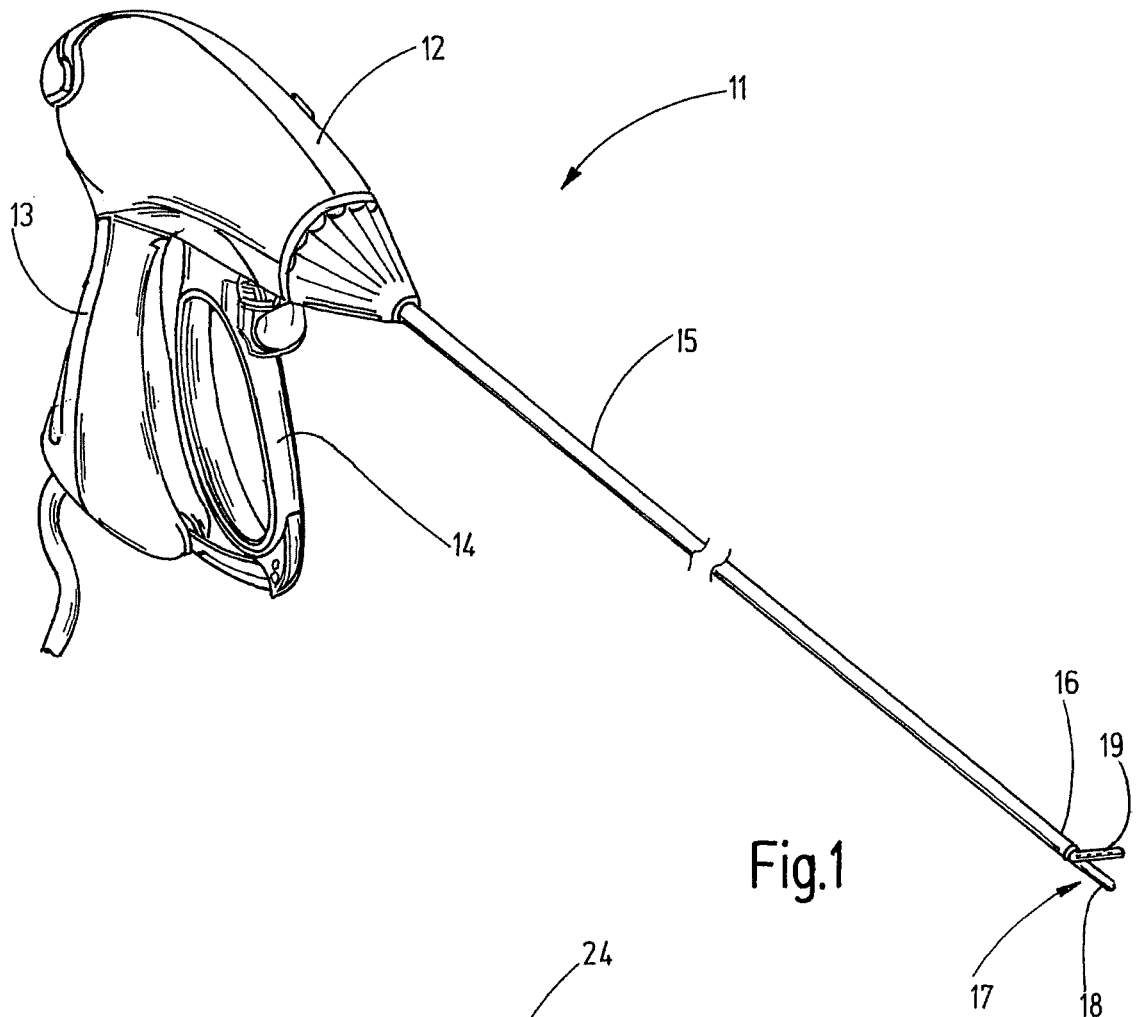
FIG. 1 a surgical instrument in an exemplary configuration and in perspective simplified illustration, FIG. 2 a tool supported by the instrument according to FIG. 1 in a simplified vertical cut illustration, FIG. 3 a cutting electrode of the tool according to FIG. 2 in a simplified perspective illustration, FIG. 4 a material blank for manufacturing a cutting electrode in a side view, FIG. 5 a mold with a material blank in explosion illustration cut orthogonal to a separation plane of the mold, FIG. 6 a material blank in partly cut illustration in the area of a rated break location, FIG. 7 an alternative embodiment of a material blank in partly cut illustration in the area of a rated break location, FIG. 8 a material blank provided with a plastic body for manufacturing of a cutting electrode, FIG. 9 a cutting electrode in a vertical partly cut illustration in a first embodiment, and FIG. 10 a cutting electrode in the illustration according to FIG. 9, however in a modified embodiment.
Figure 2:
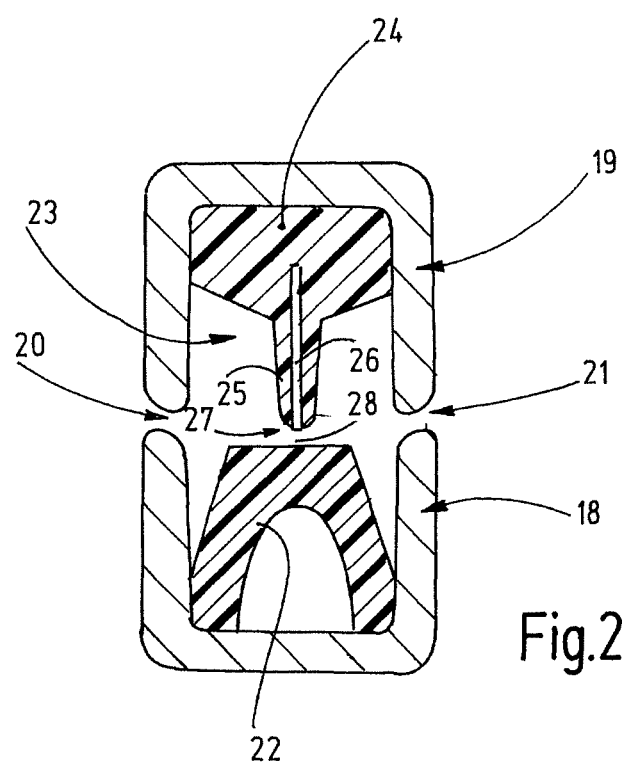
Figure 3:
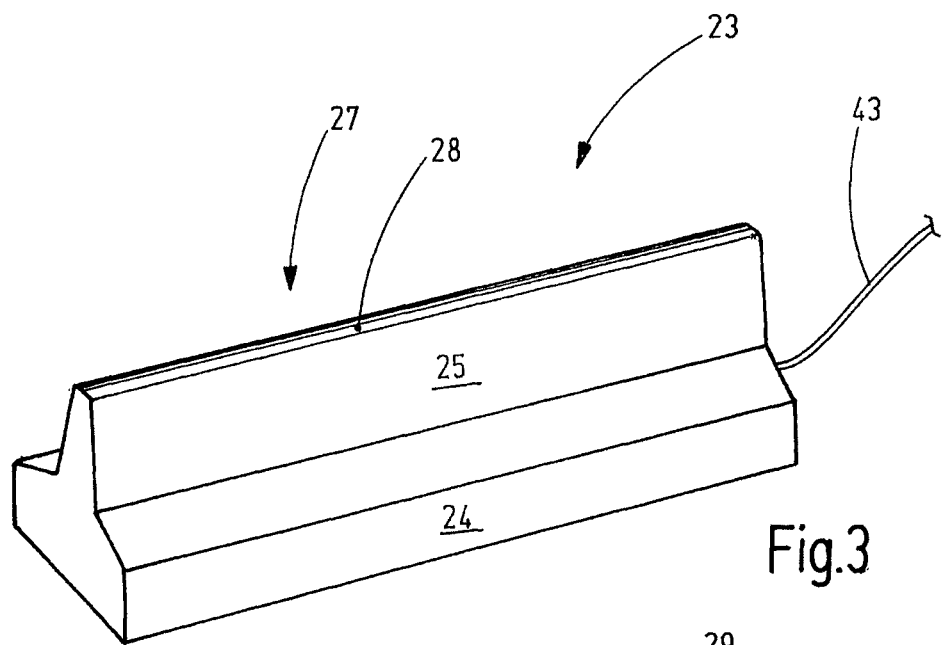

FIG. 1 illustrates a surgical instrument 11 that is particularly configured for laparascopic treatment of a patient. The instrument 11 comprises a housing 12 with a handle 13 and a hand lever 14 provided thereon. A tool 17 is supported at the distal end 16 of a shank 15 extending away from housing 12. The tool comprises a first jaw member 18 and a second jaw member 19, at least one of which is movable toward the other and away from the other by actuating the hand lever 14 in order to be able to clamp tissue in between.

The jaw members 18, 19 form a forceps-like tool 17 that is configured for tissue sealing and/or tissue cutting. For this the jaw members 18, 19 can be connected with different poles of a voltage source and thus define coagulation gaps 20, 21 between its legs as it is, for example, generally known from EP 3 132 765 A1. Between these coagulation gaps 20, 21 a preferably elastic counter support 22 and in the opposing jaw member 19 a cutting electrode 23 are arranged. It comprises a mounting or base section 24 and a wall section 25, both consisting of plastic, preferably an elastic plastic, wherein an electrode 26 preferably consisting of metal is embedded in the wall section 25 and if applicable, at least partly also extending in the base section 24. At the face side 27 only a narrow edge 28 of the electrode 26 remains uncovered. Apart therefrom the electrode 26 is embedded into the wall section 25 and the base section 24 such that it is electrically insulated.

The tool 17 can also be part of another instrument, e.g. an instrument that can be used in an endoscopic manner or an instrument configured for the open surgery use.

Figure 4:
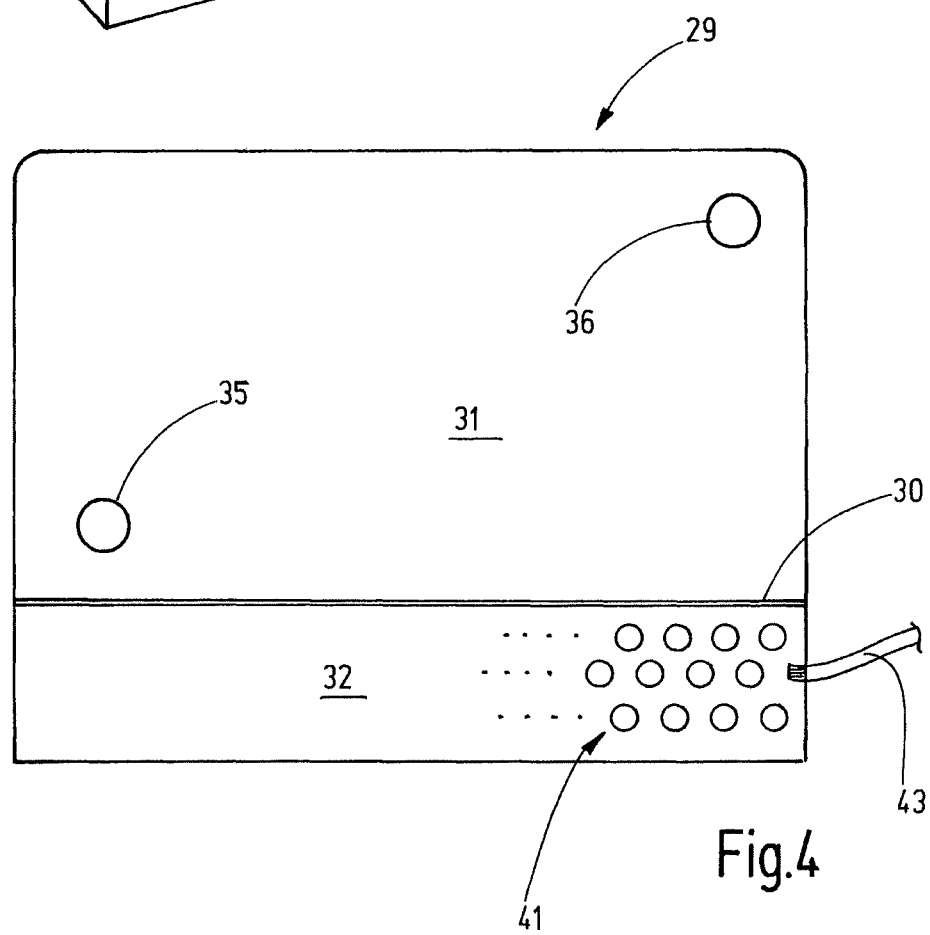

The manufacturing of the cutting electrode 23 is as follows:

Manufacturing is started with a material blank 29, as illustrated in FIG. 4. The material blank 29 consists of a suitable electrode material, e.g. a steel alloy, a titanium alloy or of an electrically conductive ceramic. Preferably the material blank 29 consists of a spring elastic material that, however, does not provide any remarkable plastic deformability. Particularly, a material is preferred a breaking point of which is reached without prior plastic deformation.

Figures 6, 7, 8:
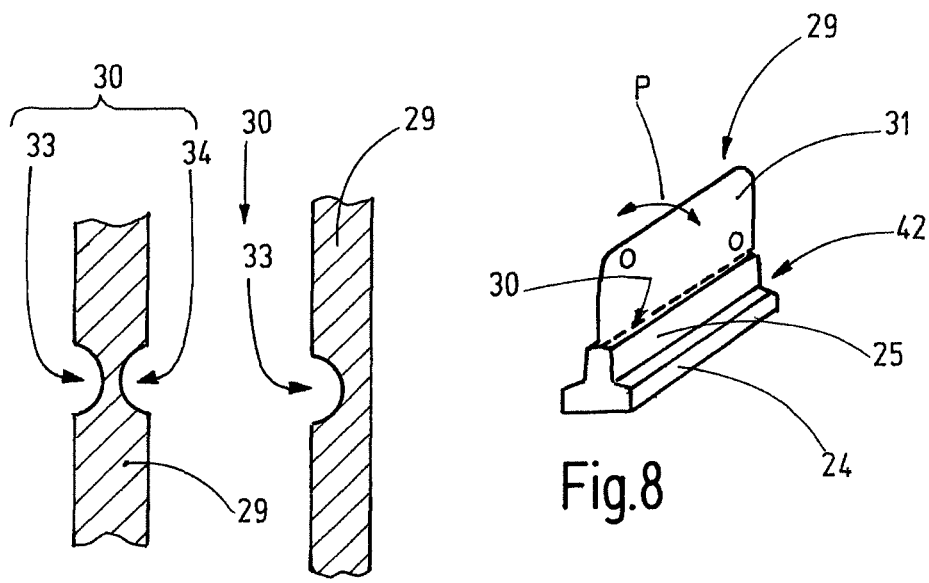

The material blank 29 is provided with a preferably line-shaped rated break location 30 that separates a first section 31 of the material blank 29 from a second section 32. The second section 32 forms the subsequent electrode 26, whereas the first section 31 serves for temporary handling only. The rated break location 30 is a line-like weakening of the material of the material blank 29, e.g. by means of a groove 33 manufactured in the material blank 29 as apparent from FIG. 7. Instead of one groove 33 that is only provided in one flat side of the material blank 29, the rated break location 30 can also be formed by two grooves 33, 34 that are provided parallel to each other in flat sides of the material blank 29 facing away from each other, as shown in FIG. 6. The two grooves 33, 34 thereby extend along same paths and are arranged in the same position.

Independent from whether only one groove 33 or two grooves 33, 34 are provided, they can be manufactured by any suitable method, e.g. by grinding, milling, embossing, roller burnishing or etching. The cross-section of the grooves 33, 34 can be created depending on the selected method and the desired edge shape as being round, angled, triangular, quadrangular, trapezoid-shaped or in a non-defined form, particularly by an etching method. However, the depth and the width of the groove are also defined by the etching method.

Figure 5:
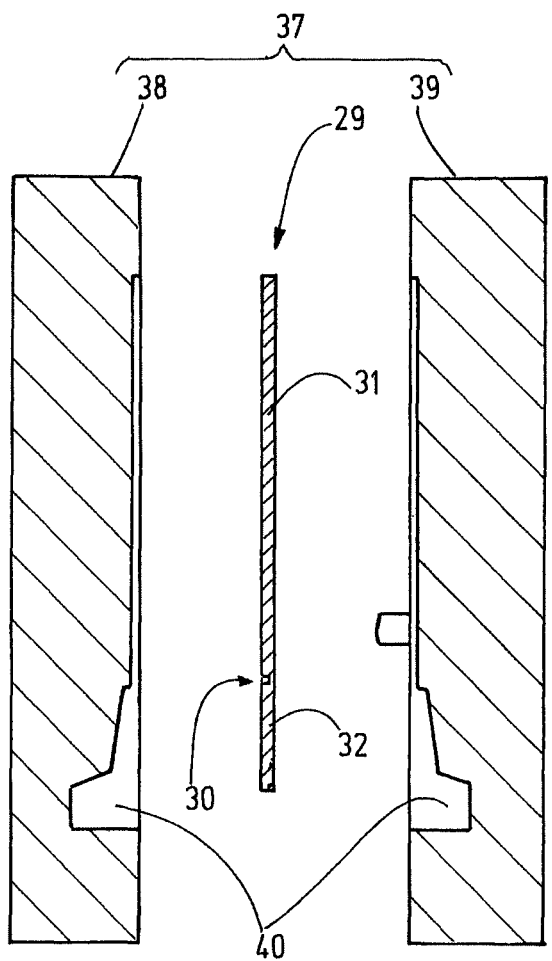

One or more positioning structures can be provided in the first section 31, e.g. in the form of positioning holes 35, 36. They can serve, for example, for positioning of the material blank 29 in a mold 37 having two mold halves 38, 39 as apparent from FIG. 5.

The mold halves 38, 39 are respectively provided with an engraving that is configured in its form and depth in the area of the first section 31 of the material blank that the material blank 29 is retained at the first section 31, if the mold 37 is closed, wherein the two mold halves 38, 39 abut two-dimensionally at the first section 31. Particularly the region of the mold halves 38, 39 holding the first section 31 terminates substantially flush at the rated break location 30. If mold 37 is closed, a hollow space 40 is thereby created around the second section 32 into which the second section 32 extends in a cantilever manner. This hollow space 40, however, terminates at flush at the rated break location 30.

For manufacturing the cutting electrode 23 with the mold 37 closed the section 32 is filled with a suitable plastic, e.g. silicone, that thereby can also pass through the holes 41 that can be configured in the second section 32 for form fit fixation of the plastic at the material blank. The shape of the holes can be round or angular.

After curing of the plastic and the opening of the mold 37 the material blank 29 with the plastic body 42 formed thereon can be removed from mold 37. As illustrated in FIG. 8, the rated break location 30 now directly adjoins the upper end of the wall section 25. A cable 43 attached to section 32 of the material blank 29 extends out of the plastic body 42 if applicable.

Figures 9, 10:
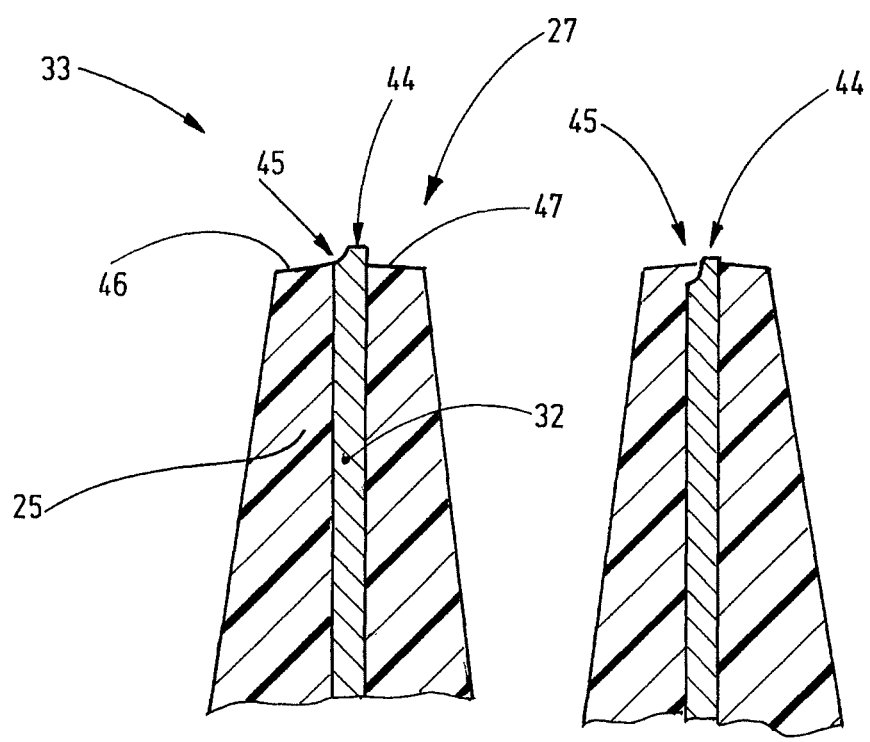

For finishing the cutting electrode 23 the first section 31 is now moved forth and back in a direction characterized by an arrow P relative to the plastic body 42, whereby the first section 31 breaks off the second section at the rated break location 30. A breaking edge 44 is thereby formed as shown in FIG. 9. From the former groove 32 a tapering section 45 is created such that the breaking edge 44 has a smaller width than the thickness of the second section 32 embedded in the plastic body. The width of the breaking edge 44, as well as the thickness of the second section 32, are measured horizontally in FIG. 9, i.e. in any case orthogonal to the flat side of the second section 32.

The wall section 25 comprises at its face side 27 on both sides of the breaking edge 44 planar or rounded surface sections 46, 47, the width thereof is preferably in each case at most ten times as large and further preferably at most three times as large or also at most two times as large as the thickness of the second section 32.

While the wall section 25 can directly adjoin the tapering section 45 at the face side, as illustrated in FIG. 9, it can also extend into the tapering section 45 according to FIG. 10 such that also the tapering section 45 can be partly or completely covered with plastic and only the breaking edge 44 remains uncovered. In so doing, a particularly high current concentration is achieved.

The breaking edge 44 can be rough due to breaking and does not need to be postprocessed. After breaking the first section 31 of the second overmolded section 32, according to FIG. 8, the cutting electrode 23 is finished and can be mounted in the instrument according to FIG. 1. At the breaking edge local current concentrations occur during cutting due to the roughness supporting the cutting. It is, however, also possible to postprocess the breaking edge, e.g. by polishing, particularly electro-polishing.

The details described in connection with FIGS. 5 and 8-10 apply similarly for material blanks 29 according to FIG. 6 and material blanks 29 according to FIG. 7.

Embodiments of the inventive method serve to manufacture a cutting electrode for a surgical instrument 11, wherein the method avoids applying of forces for separating the cross-section of the cutting electrode 23 after attachment of the plastic body at the cutting electrode 23. For manufacturing the cutting electrode 23 it is started with a material blank 29 that is provided with a rated break location 30. It is dimensioned that its separation is possible with low forces that are particularly so low, such that they can also be transmitted by the plastic body. The rated break location 30 separates the material blank 29 in a first section 31 serving exclusively for handling and positioning of the material blank 29 in a mold 37 as well as in a second section 32 that self-supportingly projects in a mold hollow space 40 and is overmolded by plastic.

After the removal the first section 31 can be easily broken off the cutting electrode 23. The created breaking edge 44 forms an ideal cutting edge.

The invention claimed is:

1. A method for manufacturing a cutting electrode for a surgical instrument, the method comprising the following steps:
   providing a material blank;
   providing a rated break location that is arranged at the material blank separating it in a first and second section, wherein the first section of the material blank is configured for temporary handling only and comprises positioning holes, wherein only the first section of the material blank includes the positioning holes;
   inserting the material blank provided with the rated break location in a mold that comprises an engraving, holding the first section with contact, and defining a hollow space around the second section, wherein the mold further comprises locating pins adapted to cooperate with the positioning holes of the first section and inserting the material blank in the mold comprises inserting the locating pins into the positioning holes of the first section;

inserting plastic in the mold for creating a plastic body that encloses only the second section and not the first section of the material blank;

opening the mold and removing the plastic body with the second section of the material blank held therein, leaving the first section of the material blank free and devoid of any plastic body; and breaking the first section off of the second section along the rated break location.

2. The method according to claim 1, wherein the first section is larger than the second section.

3. The method according to claim 1, wherein the material blank is provided with an electrical connection conductor prior to the insertion in the mold, the electrical connection conductor being provided only at the second section of the material blank.

4. The method according to claim 1, wherein the rated break location is configured as a line-like area with reduced material thickness.

5. The method according to claim 4, wherein the area with reduced material thickness is formed by at least one groove that is arranged at least one flat side of the material blank.

6. The method according to claim 5, wherein the groove is created by an etching process.

7. A cutting electrode manufactured according to a method according to claim 1, the cutting electrode comprising the plastic body in which an electrode is embedded that has a breaking edge that remains uncovered.

8. The cutting electrode according to claim 7, wherein the plastic body is made of at least one of a flexible plastic, an elastic plastic, and silicone.

9. The cutting electrode according to claim 7, wherein the electrode has a uniform constant thickness and comprises a reduced thickness in direct proximity of the breaking edge, such that a tapering section is formed adjoining the breaking edge.

10. The cutting electrode according to claim 9, wherein the plastic body is configured to extend up to the tapering section.

11. The cutting electrode according to claim 9, wherein the plastic body is configured to extend beyond in the tapering section.

12. The cutting electrode according to claim 7, wherein the cutting electrode comprises holes penetrated by plastic.

13. The cutting electrode according to claim 7, wherein a width of the breaking edge is smaller than a thickness of the electrode.

14. An instrument having the cutting electrode according to claim 7.

15. The cutting electrode according to claim 7, wherein the width of the breaking edge is less than or equal to half the thickness of the electrode.

16. The cutting electrode according to claim 7, wherein the plastic body covers a portion of a tapered cross-section of the cutting electrode.

17. The method according to claim 1, further comprising the step of planarizing the cutting electrode to have a substantially flat top surface.

18. A method for manufacturing a cutting electrode for a surgical instrument, the method comprising the following steps:

providing a material blank comprising a rated break location that separates the material blank a first section and second section, wherein the first section of the material blank is larger than the second section and is configured for temporary handling only;

inserting the material blank into a mold, the mold defining a hollow space around the second section only of the material blank;

inserting plastic in the hollow space of the mold thereby creating a plastic body that encloses only the second section of the material blank;

opening the mold and removing the plastic body with the second section of the material blank held therein, leaving the first section of the material blank free and devoid of any plastic body; and breaking the first section off of the second section along the rated break location.

19. The method according to claim 18, wherein the first section of the material blank includes positioning holes for receiving corresponding locating pins of the mold, and the second section includes through holes for receiving the plastic inserted into the mold, wherein the first section is devoid of any of the through holes, and the second section is devoid of any of the positioning holes.

* * * * *